(12) United States Patent  
Tass

(10) Patent No.: US 11,744,514 B2
(45) Date of Patent: Sep. 5, 2023

(54) DEVICE AND METHOD FOR CALIBRATING A NON-INVASIVE MECHANICALLY TACTILE AND/OR THERMAL NEUROSTIMULATION

(71) Applicant: GRETAP AG, Zug (DE)

(72) Inventor: Peter Alexander Tass, Tegernsee (DE)

(73) Assignee: GRETAP AG, Zug (CH)

( * ) Notice: Subject to any disclaimer, the term of this patent is extended or adjusted under 35 U.S.C. 154(b) by 526 days.

(21) Appl. No.: 15/548,243

(22) PCT Filed: Feb. 4, 2016

(86) PCT No.: PCT/EP2016/052389
§ 371 (c)(1),
(2) Date: Aug. 2, 2017

(87) PCT Pub. No.: WO2016/128291
PCT Pub. Date: Aug. 18, 2016

(65) Prior Publication Data
US 2018/0020972 A1 Jan. 25, 2018

(30) Foreign Application Priority Data
Feb. 9, 2015 (DE) ............ 10 2015 101 823.3

(51) Int. Cl.
*A61B 5/00* (2006.01)
*A61B 5/11* (2006.01)
(Continued)

(52) U.S. Cl.
CPC .......... *A61B 5/4836* (2013.01); *A61B 5/1101* (2013.01); *A61B 5/24* (2021.01);
(Continued)

(58) Field of Classification Search
CPC .......... A61H 2230/00; A61H 2230/105; A61H 2230/85; A61H 2230/085; A61H 2201/50;
(Continued)

(56) References Cited

U.S. PATENT DOCUMENTS

2006/0047324 A1* 3/2006 Tass ...................... A61M 21/00
607/45
2006/0212089 A1 9/2006 Tass
(Continued)

FOREIGN PATENT DOCUMENTS

| CN | 101888875 A | 11/2010 |
| CN | 102905760 A | 1/2013 |

(Continued)

OTHER PUBLICATIONS

E. Batschelet: Circular Statistics in Biology (Academic Press, London, 1981).

(Continued)

*Primary Examiner* — Joseph D. Boecker
*Assistant Examiner* — Brian T Khong
(74) *Attorney, Agent, or Firm* — ArentFox Schiff LLP

(57) ABSTRACT

A device for stimulating neurons that includes a stimulation unit that applies mechanically tactile and/or thermal stimuli to the body surface of a patient that stimulate neurons with a pathologically synchronous and oscillatory neural activity. The device includes a measuring unit that records measurement signals of neural activity of the stimulated neurons, and a controller that controls the stimulation unit and analyzes the measurement signals. The controller actuates the stimulation unit to scan at least one part of the body surface of the patient along a path and thereby periodically applies stimuli and also selects two regions or more regions on the patient's body surface along the path where the phase synchronization between the periodic application of the stimuli and the (Continued)

neural activity of the stimulated neurons have a local maximum using the measurement signals. The stimuli are then applied in a delayed manner in the two regions.

20 Claims, 7 Drawing Sheets

(51) Int. Cl.

| | | |
|---|---|---|
| A61N 1/36 | (2006.01) | |
| A61H 23/02 | (2006.01) | |
| A61B 5/24 | (2021.01) | |
| A61B 5/377 | (2021.01) | |
| A61F 7/02 | (2006.01) | |
| A61F 7/00 | (2006.01) | |
| A61N 1/04 | (2006.01) | |
| G16H 20/30 | (2018.01) | |
| A61B 5/245 | (2021.01) | |
| A61B 5/291 | (2021.01) | |
| A61B 5/369 | (2021.01) | |
| A61B 5/389 | (2021.01) | |
| A61B 5/0531 | (2021.01) | |
| A61N 5/06 | (2006.01) | |
| A61H 23/00 | (2006.01) | |
| A61N 5/067 | (2006.01) | |

(52) U.S. Cl.
CPC ............ *A61B 5/377* (2021.01); *A61B 5/4082* (2013.01); *A61F 7/02* (2013.01); *A61H 23/00* (2013.01); *A61H 23/02* (2013.01); *A61N 1/36025* (2013.01); *A61N 5/0625* (2013.01); *A61B 5/0531* (2013.01); *A61B 5/245* (2021.01); *A61B 5/291* (2021.01); *A61B 5/369* (2021.01); *A61B 5/389* (2021.01); *A61B 5/4064* (2013.01); *A61F 7/00* (2013.01); *A61F 2007/0002* (2013.01); *A61F 2007/0018* (2013.01); *A61F 2007/0022* (2013.01); *A61F 2007/0029* (2013.01); *A61F 2007/0228* (2013.01); *A61H 2201/0207* (2013.01); *A61H 2201/0228* (2013.01); *A61H 2201/10* (2013.01); *A61H 2201/165* (2013.01); *A61H 2201/5043* (2013.01); *A61H 2201/5046* (2013.01); *A61H 2201/5058* (2013.01); *A61H 2201/5082* (2013.01); *A61H 2201/5084* (2013.01); *A61H 2205/021* (2013.01); *A61H 2205/027* (2013.01); *A61H 2205/06* (2013.01); *A61H 2205/08* (2013.01); *A61H 2205/083* (2013.01); *A61H 2230/08* (2013.01); *A61H 2230/085* (2013.01); *A61H 2230/10* (2013.01); *A61H 2230/105* (2013.01); *A61H 2230/60* (2013.01); *A61H 2230/605* (2013.01); *A61N 1/0476* (2013.01); *A61N 5/067* (2021.08); *A61N 2005/063* (2013.01); *G16H 20/30* (2018.01)

(58) Field of Classification Search
CPC .... A61H 2201/5002; A61H 2201/5005; A61H 2201/5007; A61H 2230/08; A61H 2230/10; A61H 23/00; A61H 23/006; A61H 23/02–04; A61B 5/0048; A61B 5/4836; A61N 1/36–3718
See application file for complete search history.

(56) References Cited

U.S. PATENT DOCUMENTS

| | | | |
|---|---|---|---|
| 2010/0168816 A1* | 7/2010 | Tass | A61N 1/0529 607/45 |
| 2011/0009921 A1 | 1/2011 | Tass et al. | |
| 2011/0201977 A1 | 8/2011 | Tass | |
| 2013/0041296 A1* | 2/2013 | Tass | A61H 23/0254 601/15 |
| 2013/0066392 A1 | 3/2013 | Simon et al. | |
| 2013/0090519 A1* | 4/2013 | Tass | A61M 21/00 600/28 |
| 2013/0158451 A1 | 6/2013 | Juto et al. | |
| 2015/0105844 A1* | 4/2015 | Tass | A61N 5/0625 607/90 |
| 2015/0238104 A1* | 8/2015 | Tass | A61B 5/4064 600/409 |
| 2015/0297444 A1* | 10/2015 | Tass | A61H 23/00 601/47 |
| 2016/0175557 A1* | 6/2016 | Tass | A61M 21/00 600/28 |

FOREIGN PATENT DOCUMENTS

| | | | |
|---|---|---|---|
| CN | 103608070 A | | 2/2014 |
| CN | 103917165 A | | 7/2014 |
| CN | 104144729 A | | 11/2014 |
| CN | 104203345 A | | 12/2014 |
| DE | 10 2012 005 030 A1 | | 9/2013 |
| WO | WO 2011/127918 A1 | | 10/2011 |
| WO | WO 2013/117655 A1 | | 6/2013 |
| WO | WO-2013117655 A1 | * | 8/2013 |
| WO | WO 2013/135685 A1 | | 9/2013 |

OTHER PUBLICATIONS

M. G. Rosenblum, A. S. Pikovsky, C. Schäfer, J. Kurths. P. A. Tass: Phase Synonromizaton: From Theory to Data Analysis. In: Mass F. (Ed.): Handbook of Biological Physics, Elsevier (2000).

N. E. Huang et al.: A confidence limit for the empirical mode decomposition and Hilbert spectral analysis. Proceedings of the Royal Society of London Series A 459, 2317-2345 (2003).

N. E. Huang et al.: The empirical mode decomposition and the Hilbert spectrum for nonlinear and non-stationary time series analysis. Proc. R. Soc. A: Math. Phys. Eng. Sci. 454, 903-995 (1998).

N. H. Kuiper: Tests concerning random points in a circle. Proc. K. Ned. Akad. Wet., Ser. A: Math. Sci. 63. 38 (1960).

P. A. Tass: Stochastic chase resetting of two coupled phase oscillators stimulated at different times, Physical Review E 67, 051902-1 bis 051902-15 (2003).

P. A. Tass: Transmission of stimulus-tocked resnonses in two coupled phase oscillators. Phys. Rev. E 69, 051909-1-24 (2004).

P. Landa: Nonlinear Oscillations and Waves in Dynamical Systems. Kluwer Academic Publishers, Dordrecht-Boston-London, 1996.

PA Tass: Effective desynchronization with a stimulation technique based on soft pnase resetting, Europhys. Lett. 57 (2), 164-170 (2002).

Tass, M.G. Rosenblum, J. Weule, J. Kurths, A. Pikovsky, J. Volkmann, A. Schnitzler und H.-J. Freund: Detection of n:m Phase Locking from Noisy Data: Application to Magnetoencephalography. Phys. Rev. Lett. 81 (15), 3291-3294(1998).

* cited by examiner

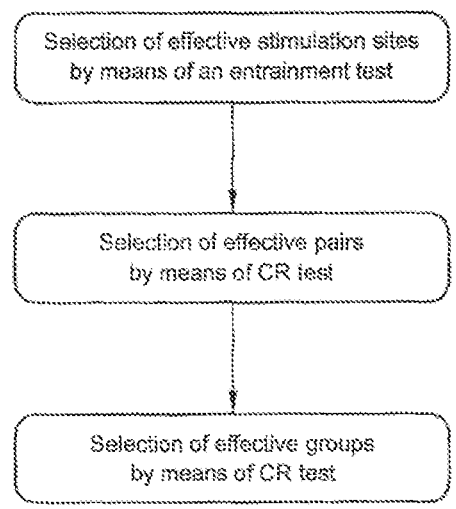
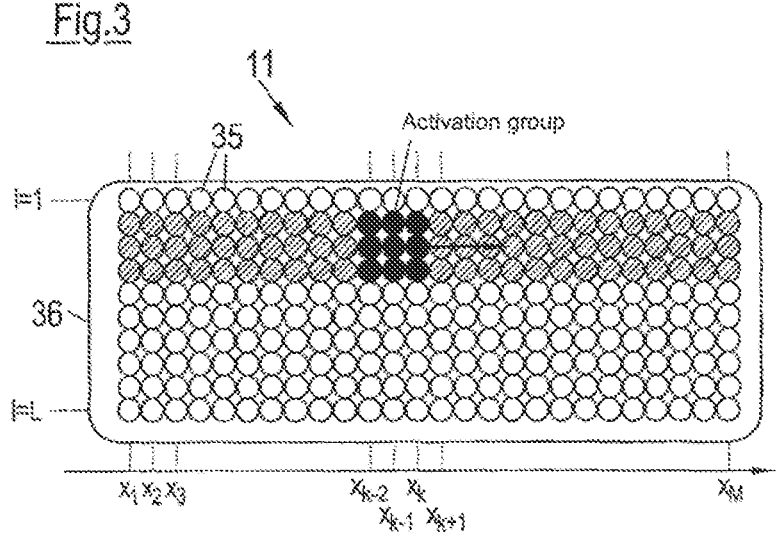

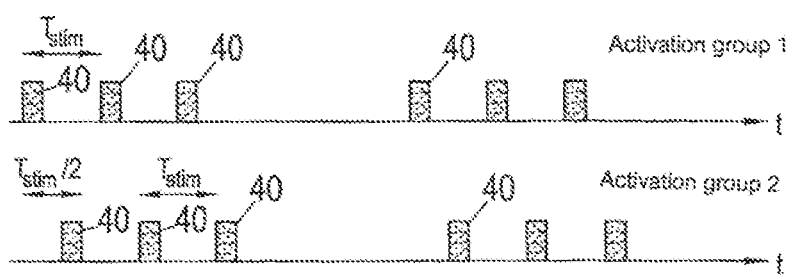
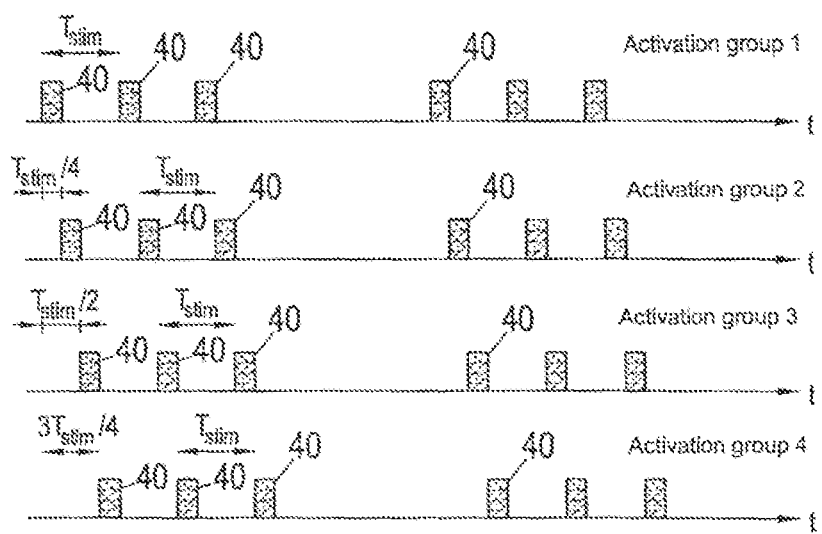

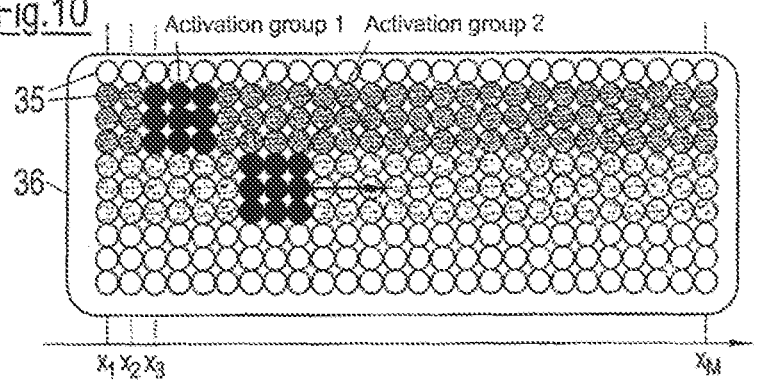
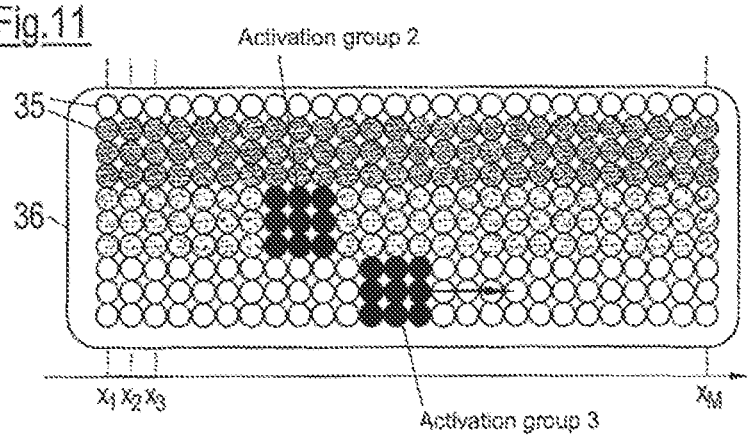
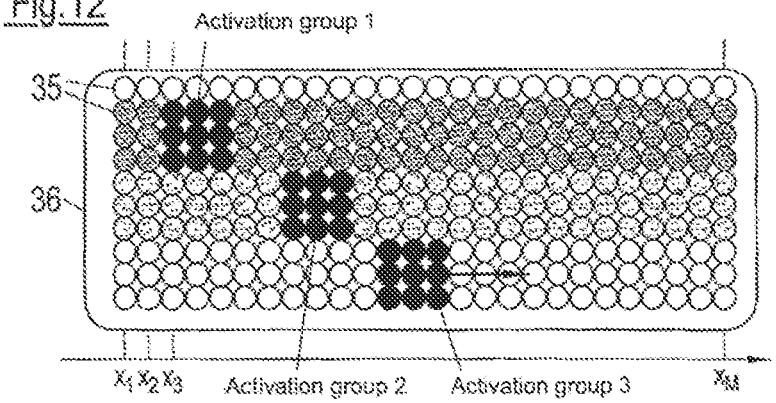

DEVICE AND METHOD FOR CALIBRATING A NON-INVASIVE MECHANICALLY TACTILE AND/OR THERMAL NEUROSTIMULATION

CROSS-REFERENCE TO RELATED APPLICATIONS

This application is a National Stage entry of International Application No. PCT/EP2016/052389, filed Feb. 4, 2016, which claims priority to German Patent Application No. 10 2015 101823.3 filed Feb. 9, 2015, the disclosures of these priority applications are incorporated in their entirety herein by reference.

TECHNICAL FIELD

The invention relates to an apparatus and to a method for calibrating a non-invasive mechanically tactile and/or thermal neurostimulation.

BACKGROUND

Nerve cell assemblies in the circumscribed regions of the brain are pathologically, e.g. excessively synchronously, active in patients with neurological or psychiatric diseases such as Parkinson's disease, essential tremor, tinnitus, dystonia or obsessive compulsive disorders. In this case, a large number of neurons synchronously form action potentials, i.e. the participating neurons fire excessively synchronously. In a healthy person, in contrast, the neurons fire with a different quality, e.g. in an uncorrelated manner, in these brain sectors.

Stimulation techniques have been developed for treating such diseases which directly counteract pathologically synchronous neuronal activity. Coordinated reset (CR) stimulation is in this respect characterized by high therapeutic effectiveness and safety. Non-invasive CR stimulation can be implemented with different stimulus modalities: by means of sensory, e.g. vibrotactile, stimuli; by means of electrical or magnetic stimulation or ultrasound stimulation; or by means of direct electrical or magnetic stimulation or ultrasound stimulation of the brain or spinal cord.

Mechanically tactile, in particular vibrotactile, CR stimulation can e.g. be used for treating Parkinson's disease. Further indications are e.g. represented by epileptic fits (by means of vibrotactile CR stimulation), functional disorders after stroke (by means of vibrotactile CR stimulation), chronic pain syndromes (by means of vibrotactile and/or thermal CR stimulation), and migraines (e.g. by means of visual CR stimulation). These diseases and other brain diseases can furthermore be treated by transcranial magnetic stimulation or by direct electrical stimulation of the brain or direct brain stimulation by means of ultrasound.

The non-invasive CR stimulation apparatus and methods are much lower in side effects and are much less expensive than invasive CR stimulation apparatus and methods and are thus accessible for a larger number of patients.

SUMMARY

It is of central importance for the effectiveness of CR stimulation that (i) the stimuli applied actually reach the neuronal populations to be simulated in an invasive or non-invasive manner, i.e. stimulation does not take place at incorrect sites of the body; and that (ii) this stimulation takes place at sufficiently different sites of the body so that sufficiently different neuronal subpopulations are stimulated. In invasive CR stimulation, the ideal localization of the implanted electrode is ensured within the framework of the surgical planning inter alia via detailed anatomical information, e.g. from magnetic resonance imaging examinations. In non-invasive stimulation methods in contrast, the calibration of the localization of the different non-invasive actuators, e.g. of the positioning of the mechanically tactile or thermal stimulators on the skin in relation to the affected body part, has been a problem up to now.

It is the underlying object of the invention to provide an apparatus and a method which allow a calibration of the stimulation parameters independent of the examiner, carried out automatically and on an electrophysiological basis. Suitable regions on the surface of the body of the patient for the mechanically tactile and/or thermal stimulation should in particular be determined fast and reliably to be able to stimulate suitable target sites in the brain so that the CR stimulation is effective. The invention should furthermore make it possible (i) to carry out the therapy effectively; (ii) to avoid side effects; and (iii) to make the examination to be carried out for the parameter setting as short, practical and tolerable as possible for the patient.

The object underlying the invention is satisfied by the features of the independent claims. Advantageous further developments and aspects of the invention are set forth in the dependent claims.

BRIEF DESCRIPTION OF THE DRAWINGS

The invention will be explained in more detail in the following in an exemplary manner with reference to the drawings. There are shown in these:

FIG. 2 illustrates a flowchart for illustrating the calibration of the apparatus shown in FIG. 1;

FIGS. 3 and 4 illustrate schematic representations of a cuff having an array of stimulation elements and an activation group migrating over the cuff;

FIG. 8 illustrates a schematic representation of a CR stimulation using two activation groups;

FIG. 9 illustrates a schematic representation of a CR stimulation using four activation groups;

FIG. 10 illustrates a schematic representation of a determination of the ideal spacing between two activation groups;

FIG. 11 illustrates a schematic representation of a pairwise testing of activation groups;

FIG. 12 illustrates a schematic representation of an iterative testing of activation groups;

DETAILED DESCRIPTION

Figure 1:
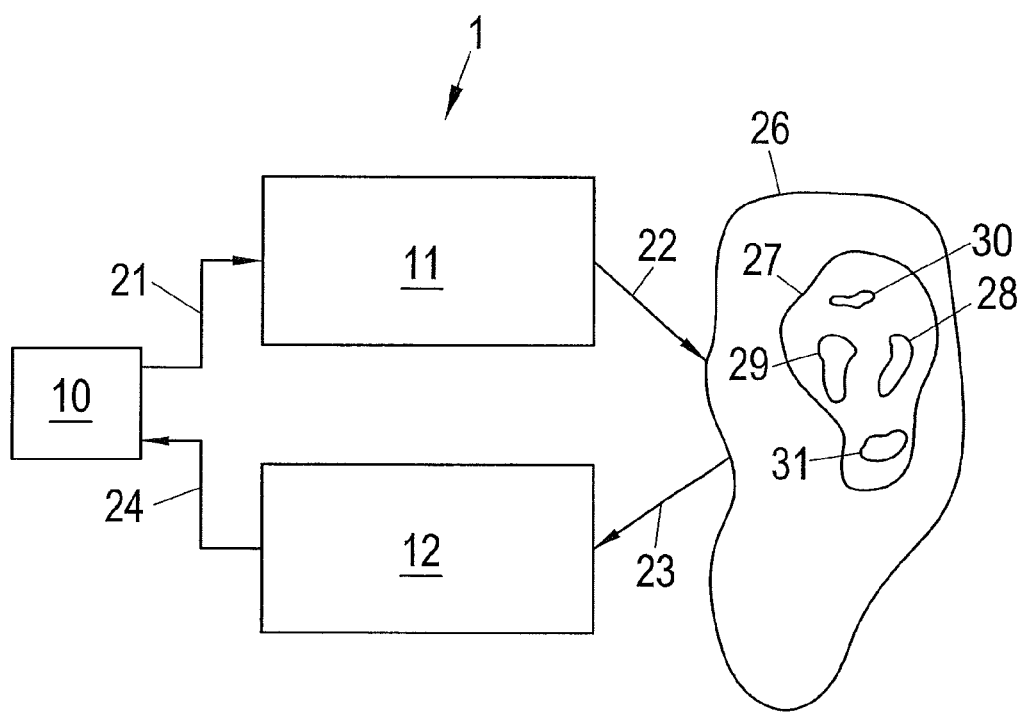
FIG. 1 illustrates a schematic representation of an apparatus for the mechanically tactile and/or thermal desynchronizing neurostimulation during operation.

An apparatus 1 for stimulating neurons having a pathologically synchronous and oscillatory neuronal activity is shown schematically in FIG. 1. Stimulation parameters of a non-invasive neurostimulation can be calibrated with the aid of the apparatus 1. The pathologically synchronous and oscillatory neuronal activity can furthermore be suppressed and in particular desynchronized. The apparatus 1 comprises a control and analysis unit 10, a stimulation unit 11 and a measuring unit 12. During the operation of the apparatus 1, the control and analysis unit 10 inter alia carries out a control of the stimulation unit 11. For this purpose, the control and analysis unit 10 generates control signals 21 which are received by the stimulation unit 11. The stimulation unit 11, that can in particular include a plurality of stimulation elements, generates stimuli 22 using the control signals 21, the stimuli being administered to the patient. The stimuli 22 can be mechanically tactile stimuli and/or thermal stimuli, with the mechanically tactile stimuli in particular being able to be tactile, vibratory or vibrotactile stimuli or proprioceptive stimuli applied over the skin. The stimuli 22 can in particular be consciously perceivable by the patient. The stimulus unit 11 and in particular also the control and analysis unit 10 are non-invasive units, i.e. they are located outside the body of the patient during the operation of the apparatus 1 and are not surgically implanted in the body of the patient.

The stimulation effect achieved by the stimuli 22 is monitored with the aid of the measuring unit 12. The measuring unit 12 records one or more measured signals 23 measured at the patient, converts them as required into electrical signals 24 and supplies them to the control and analysis unit 10. The pathologically neuronal activity in the stimulated target zone or in a zone associated with the target zone can in particular be measured by means of the measuring unit 12, with the neuronal activity of this zone correlating sufficiently closely with the neuronal activity of the target zone (e.g. muscle activity). The control and analysis unit 10 processes the signals 24, e.g. the signals 24 can be amplified and filtered, and analyzes the processed signals 24. The control and analysis unit 10 in particular controls the stimulation unit 11 with reference to the results of this analysis. The control and analysis unit 10 can include e.g. a processor, e.g. a microcontroller, for carrying out its work. The stimulation processed described herein can be stored as software code in a memory associated with the control and analysis unit 10.

The measuring unit 12 includes one or more sensors that measure signals that in particular make it possible with the aid of a suitable data analysis (a) to demonstrate a phase locking, i.e. a phase synchronization, between a pulse train that is strictly periodic (with respect to the timing), on the one hand, and the phase of the pathological oscillatory activity, on the other hand; and (b) to demonstrate a decrease or increase in the amplitude of the pathological oscillatory activity. In an embodiment, the sensors of the measuring unit 12 furthermore make it possible (c) to demonstrate a stimulus-induced reset of the phase of the pathological oscillatory activity.

Non-invasive sensors can be used as the sensors, e.g. chronically or intermittently used electroencephalography (EEG) electrodes or electromyography (EMG) electrodes or magnetoencephalography (MEG) sensors (SQUIDS, i.e., superconducting quantum unit interference devices). The neuronal activity can also be determined indirectly by measuring the tremor or by measuring movements by means of accelerometers or gyroscopes or by measuring the activation of the autonomous nervous system by means of a measurement of the skin resistance. Mental state values that can be input into portable devices, e.g. smartphones, by the patient can also be used to monitor the stimulation success.

Alternatively, the sensors can be implanted in the body of the patient. Epicortical electrodes, deep brain electrodes for the measurement of e.g. local field potentials (LFPs), subdural or epidural brain electrodes, subcutaneous EEG electrodes and subdural or epidural spinal cord electrodes can, for example, serve as invasive sensors. Furthermore, electrodes to be fastened to peripheral nerves can be used as sensors.

Provision can by all means be made that the individual components of the apparatus 1, in particular the control and analysis unit 10, the stimulation unit 11 and/or the measuring unit 12, are separate from one another construction-wise. The apparatus 1 can therefore also be understood as a system.

The apparatus 1 can in particular be used for treating neurological or psychiatric diseases, e.g. Parkinson's disease, essential tremor, tremor resulting from multiple sclerosis as well as other pathological tremors, dystonia, epilepsy, depression, chronic pain syndromes, locomotor disorders, cerebellar diseases, obsessive compulsive disorders, dementia, Alzheimer's, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, cluster headache, general headache, neuralgia, ataxia, tic disorder or hypertension as well as further diseases which are characterized by pathologically increased neuronal synchronization.

The aforesaid diseases can be caused by a disorder of the bioelectrical communication of neuronal assemblies which are connected in specific circuits. In this respect, a neuronal population continuously generates pathological neuronal activity and possibly a pathological connectivity associated therewith (network structure). In this respect, a large number of neurons synchronously form action potentials, i.e. the participating neurons fire excessively synchronously. In addition, there is the fact that the pathological neuronal population has an oscillatory neuronal activity, i.e. the neurons fire rhythmically. In the case of neurological or psychiatric diseases, the mean frequency of the pathological rhythmic activity of the affected neuronal assemblies lies approximately in the range from 1 to 30 Hz, but can also be outside this range. In healthy people, the neurons fire qualitatively differently, however, e.g. in an uncorrelated manner.

The apparatus 1 is shown during a CR stimulation in FIG. 1. At least one neuronal population 27 in the brain or in the spinal cord (either of which is noted by reference 26 as shown in FIG. 1, for example) of the patient has a pathologically synchronous and oscillatory neuronal activity as described above. The stimulation unit 11 administers the stimuli 22 to the patient such that the stimuli 22 are received via receptors and are forwarded from there via the nervous system to the pathologically active neuronal population 27 in the brain and/or spinal cord 26. The stimuli 22 are designed such that the pathologically synchronous activity of the neuronal population 27 is desynchronized as the result of the stimulation. A lowering of the coincidence rate of the neurons effected by the stimulation can result in a lowering of the synaptic weights and thus in an unlearning of the tendency to produce pathologically synchronous activity.

The mechanically tactile and/or thermal stimuli 22 applied by the stimulation unit 11 are received by receptors disposed in or under the skin and are forwarded to the nervous system. These receptors include, for example, Merkel cells, Ruffini corpuscles, Meissner's corpuscles and hair follicle receptors which in particular act as receptors for the tactile stimuli 22. The vibratory stimuli 22 are predominantly directed to proprioception. The vibratory stimuli 22 can be received by receptors disposed in the skin, in the muscles, in the subcutaneous tissue and/or in the sinews of the patient. Vater-Pacini corpuscles can be named by way of example as receptors for the vibratory stimuli 22 which communicate vibration perceptions and accelerations. The thermal stimuli 22 are received by the thermoreceptors of the skin. They are warm receptors (also called heat receptors, warm sensors or heat sensors) and cold sensors (also called cold receptors). The cold sensors are more superficial in the skin of people; the heat receptors somewhat lower.

The direct stimulation of specific regions of the brain or of the spinal cord is made possible by the somatotopic association of body regions with these regions. Due to the somatotopic structure of the neural pathways and associated brain areas, different neurons are stimulated by mechanically tactile and/or thermal stimuli that are applied at different points of the body surface. The stimulation elements can be attached, for example, to the foot, lower leg and upper leg or to the hand, the lower arm and upper arm of the patient in order thereby to be able to stimulate specific neurons.

The stimulation unit 11 can accordingly separately stimulate different regions of the brain and/or spinal cord 26 in that the applied stimuli 22 are forwarded via neural conductors to different target zones which lie in the brain and/or spinal cord 26. The target zones can be stimulated with possibly different and/or time-offset stimuli 22 during the stimulation.

In the CR stimulation, stimuli 22 which effect a reset of the phase of neuronal activity of the stimulated neurons in the neuronal population 27 are administered to the neuronal population 27 which has a pathologically synchronous and oscillatory neuronal activity. The phase of the stimulated neurons is set to or close to a specific phase value, e.g. 0°, independently of the current phase value by the reset (it is not possible in practice to set a specific phase value exactly; however, this is also not required for a successful CR stimulation). The phase of the neuronal activity of the pathological neuronal population 27 is thus monitored by means of a direct stimulation. Since it is furthermore possible to stimulate the pathological neuronal population 27 at different sites, the phase of the neuronal activity of the pathological neuronal population 27 can be reset at the different stimulation sites at different points in time. As a result, the pathological neuronal population 27 whose neurons were previously synchronous and active at the same frequency and phase is split into a plurality of subpopulations which are shown schematically in FIG. 1 and are marked by the reference numerals 28, 29, 30 and 31 (four subpopulations are shown by way of example here). Within one of the subpopulations 28 to 31, the neurons are still synchronous after the resetting of the phase and also still fire at the same pathological frequency, but each of the subpopulations 28 to 31 has the phase with respect to their neuronal activity which was enforced by the stimulation stimulus. This means that the neuronal activities of the individual subpopulations 28 to 31 still have an approximately sinusoidal curve at the same pathological frequency, but different phases, after the resetting of their phases.

Due to the pathological interaction between the neurons, the state with at least two subpopulations generated by the stimulation is unstable and the total neuronal population 27 fast approaches a state of complete desynchronization in which the neurons fire without correlation. The desired state i.e. the complete desynchronization, is thus not immediately present after the time-offset (or phase-shifted) application of the phase-resetting stimuli 22, but is usually adopted within a few periods or even in less than one period of the pathological frequency.

One theory for explaining the stimulation success is based on the fact that the ultimately desired desynchronization is only made possible by the pathologically increased interaction between the neurons. In this respect, a self-organization process is made use of which is responsible for the pathological synchronization. It also has the effect that a division of an overall population 27 into subpopulations 28 to 31 with different phases is followed by a desynchronization. In contrast to this, no desynchronization would take place without a pathologically increased interaction of the neurons.

Furthermore, a reorganization of the connectivity of the disturbed neuronal networks can be achieved by the CR stimulation so that long-continuing therapeutic effects can be brought about. The obtained synaptic conversion is of great importance for the effective treatment of neurological or psychiatric diseases.

In the following, a calibration is described which is carried out using the apparatus 1 in order thus to determine the ideal stimulus parameters for the non-invasive CR stimulation.

In accordance with an embodiment, a so-called entrainment test is first carried out. For this purpose, the control and analysis unit 10 controls the stimulation unit 11 such that the stimulation unit 11 scans at least a part of the surface of the body of the patient along a path and in so doing periodically applies stimuli 22, i.e. the periodic stimuli 22 are not stationary, but rather "migrate" over the surface of the body during the scan. The control and analysis unit 10 selects at least two regions on the surface of the body of the patient along the path with reference to the measured signals 23 recorded in response to the periodic application of the stimuli 22, with the phase synchronization between the periodic application of the stimuli 22 and the neuronal activity of the stimulated neurons respectively having a local maximum in said regions. A CR stimulation is subsequently carried out at the at least two selected regions. For this purpose, the control and analysis unit 10 controls the stimulation unit 11 such that it applies stimuli 22 in the at least two selected regions that effect a phase reset of the neuronal activity of the stimulated neurons. The stimuli 22 applied in the at least two regions are offset in time with respect to one another.

The above embodiment can be further developed in that further steps are added to the calibration that are summarized in the flow chart of FIG. 2. For this purpose, the above-described entrainment test is carried out in a first step. A pair test is then carried out in a second step in which stimuli are applied at two different sites to select one or more active pairs for the CR stimulation. Finally, in a third step, a group test is carried out that provides the application of stimuli at least two, and typically more than two, different sites.

The apparatus 1 makes possible a calibration of the stimulation parameters that is independent of the examiner, is carried out automatically, has an electrophysiological base and manages with substantially lower stimulus strengths in comparison with conventional calibrations. The phase entrainment used here is a dynamic process that is effective at very low stimulus strengths. Weaker stimuli have the advantage that the calibration carried out using these stimuli is much more exact. The reason for this is that the weaker stimuli are anatomically more selective since they reach fewer neurons, namely only those that are ideally suited to the applied stimulus (and not adjacent neuronal populations in the brain that are co-stimulated as the stimulus strength increases). The calibration is carried out at a stimulus intensity at which the therapy is also actually carried out. Weaker stimuli are furthermore less stressful for patients, in particular pain patients. For example, even lighter contacts or heat stimuli of patients with chronic pain syndromes, e.g. with Sudeck's disease or neuralgias, can already be perceived as unpleasant or even painful.

Furthermore, the calibration carried out using the apparatus 1 is considerably faster in comparison with conventional calibrations. This prevents fatigue of the patient and the associated deterioration of the quality of the data, i.e. of the results. It is thereby considerably more pleasant for the patient, does not require any unreasonable compliance (co-operation of the patient) and is easy to use in practice.

In summary, the apparatus 1 makes it possible (i) to carry out the therapy effectively; (ii) to avoid side effects; and (iii) to make the examinations to be carried out for the parameter setting as short, practical and tolerable as possible for the patient.

The individual steps to be carried out for the calibration of the stimulation parameters will be explained in more detail in the following. This will be done using an embodiment of the stimulation unit 11 that is shown schematically in FIG. 3. The stimulation unit 11 here comprises an array of stimulation elements 35. Each of the stimulation elements 35 can generate mechanically tactile and/or thermal stimuli. The stimulation elements 35 in the present embodiment are components of a cuff 36 that can be fastened to a body part of the patient, for example to an arm, for the stimulation. In FIG. 3, l and m stand for the rows or columns of the array of stimulation elements 35, where l=1, . . . , L and m=1, . . . , M. The array consequently comprises L×M stimulation elements 35 in total. Each of the stimulation elements 35 can be individually controlled by the control and analysis unit 10.

The cuff 36 having the array of stimulation elements 35 makes it possible to apply stimuli periodically, wherein the points at which the stimuli are applied can change continuously. In this manner, larger parts of the surface of the body can be scanned such that suitable regions and distances between these regions can be determined for the therapeutic multi-channel stimulation by means of an analysis of the reinduced neuronal activity.

In principle, corresponding actuators could naturally also slide over the surface of the body for this purpose. It is, however, simpler to fix larger arrays of stimulation elements 35 to the body of the patient, e.g. by means of the cuff 36, and to temporally vary the activated groups of stimulation elements 35. The stimulation elements 35 can e.g. be controlled by the control and analysis unit 10 such that the activation of the stimulation elements 35 e.g. migrates along the cuff 36.

The migratory activation of a 3×3 group of stimulation elements 35 is shown by way of example in FIG. 3. The stimulation elements 35 in the lines second from the top to fourth from the top, that are highlighted by hatching, so-to-say form the path along which the activation of the stimulation elements 35 migrates. The direction of movement is shown by an arrow. The stimulation elements 35 activated at a specific point in time form a 3×3 group and are shown in black. The activation group corresponds to a region on the surface of the body of the patient that is stimulated by the stimulation elements 35 encompassed by the activation group. Only stimulation elements 35 that are at least partly disposed within the 3×3 shape of the activation group generate stimuli in the present embodiment. All the other stimulation elements 35, i.e. those stimulation elements that are disposed completely outside the 3×3 shape of the activation group, do not generate any stimuli. When the activation group migrates over the cuff 36, the region in which mechanically tactile and/or thermal stimuli are generated migrates in a corresponding manner over the surface of the body of the patient.

We designate the position of the front of the migrating 3×3 activation group by $X_F$. The front, and thus the total 3×3 activation, can e.g. migrate at a constant speed from the left end of the cuff 36 to the right end of the cuff 36. The front is at $x_k$ in FIG. 3. The invention will be explained in the following with reference to the implementation with vibrotactile stimulation elements 36. In this case, each stimulation element 36 is a respective actuator that is attached to the surface of the body and that can be deflected from its position of rest to press into the surface of the body and thereby to generate the desired stimulus.

The amplitude of the stimulation elements 36, i.e. of the actuators, used for the vibrotactile stimulation at the time t is designated by $A_{l,m}(t)$. The amplitude of the vibration of the stimulation elements 36 thus reads as follows in the kth column i.e. at $x_k$, in the second from top to fourth from top lines:

$$\text{For } X_F(t) \leq x_{k-1}: A_{l,k}(t) = 0$$

$$\text{For } x_{k-1} < X_F(t) \leq x_k: A_{l,k}(t) = A_{max} \frac{X_F(t) - x_{k-1}}{x_k - x_{k-1}}$$

$$\text{For } x_k \leq X_F(t) \leq x_{k+3}: A_{l,k}(t) = A_{max}$$

$$\text{For } x_{k+3} < X_F(t) < x_{k+4}: A_{l,k}(t) = A_{max}\left(1 - \frac{X_F(t) - x_{k+3}}{x_{k+4} - x_{k+3}}\right)$$

$$\text{For } X_F(t) \geq x_{k+4}: A_{l,k}(t) = 0$$

$$\text{where } 1 = 2, 3, 4.$$

Figure 4:
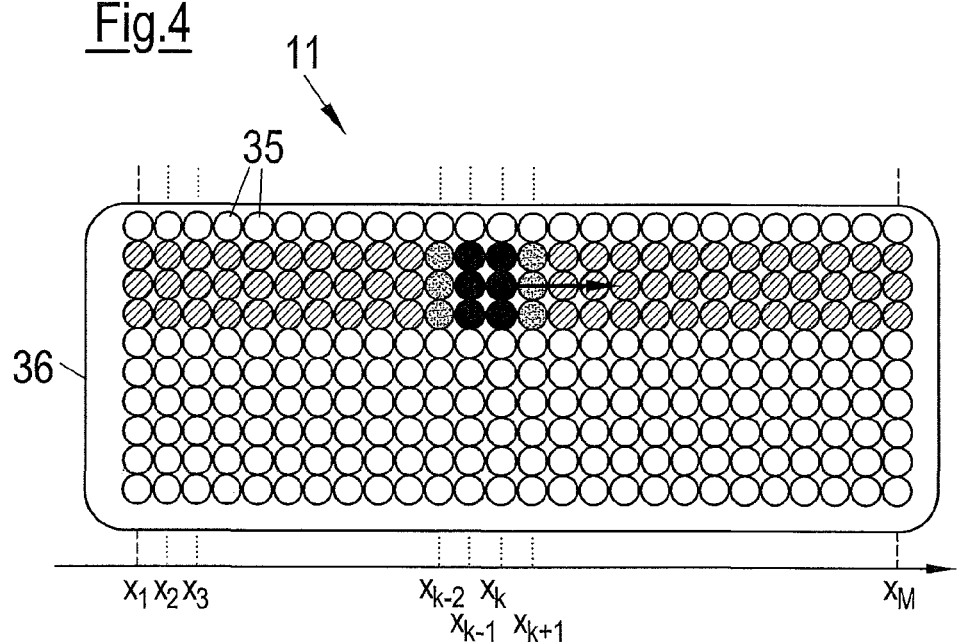

In FIG. 4, the activation of a 3×3 group of stimulation elements 36 has already migrated half a step further to the right in comparison with FIG. 3. The vibration amplitude of the right and left vertical groups of three of the migrating activation is not at a maximum due to interpolation (shown in dark gray).

Non-linear interpolation methods can also be used in addition to the linear interpolation used here. Instead of the front $X_F(t)$, the position of the focus of the group activation can e.g. also be analogously observed; it is at $x_{k-1}$ in FIG. 3.

While the activation front $X_F(t)$ migrates slowly at constant speed from left to right along the cuff 36, e.g. from the wrist to the elbow, a periodic sequence P(t) of stimuli is applied. The periodic sequence P(t) is shown schematically in FIG. 5. This sequence is typically, inter alia due to the inertia of the actuators, a smoother, non-rectangular sequence. To determine the temporal pattern of the vibration amplitude of a specific actuator, the product of the global period sequence P(t) and the local amplitude $A_{l,m}(t)$, that is $P(t)A_{l,m}(t)$, is calculated. The total vibration of a specific actuator is consequently $P(t)A_{l,m}(t)V(t)$, where V(t) is a high-frequency vibration, that is e.g. a sine oscillation or a rectangular oscillation at a frequency of, for example, 250 Hz. V(t) can also be a low-frequency sine oscillation or rectangular oscillation in the range from 0.25 to 50 Hz. In a further embodiment, the actuators (or vibrators) can also be pressed into the skin—triggered by P(t)—such that the actuators deflected in this manner do not oscillate (vibrate) around the zero line, but rather around the deflection $P_0$. In this case, the total vibration signal e.g. reads $P(t)[A_{l,m}(t)V(t)+P_0]$.

$A_{l,m}(t)$ consequently indicates the amplitude of each actuator (with a respective l, m) at a given point in time t. $A_{l,m}(t)$ furthermore indicates the site at which the activated group of actuators shown by way of example in FIG. 3 is located at the respective point in time t.

Figure 5:
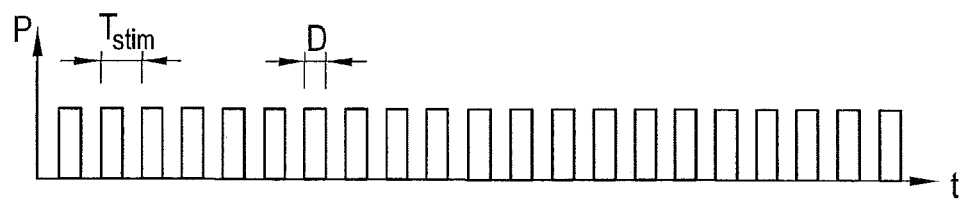
FIG. 5 illustrates a schematic representation of a periodic sequence of stimuli.

P(t) comprises a periodic sequence of pulses. The pulses determine the periods of time at which stimuli are applied. No stimuli are applied during the periods of time between the pulses when P(t) is equal to zero. As FIG. 5 shows, the periodic sequence P(t) has the period $T_{stim}$. The stimulation frequency $f_{stim}=1/T_{stim}$ is typically in the range from 0.25 to 30 Hz. The duration $D_{stim}$ of the pulses, i.e. the duration of a stimulation interval, can lie in the range from 10 to 1000 ms. The pulses of the periodic sequence P(t) can in particular be identical.

The period $T_{stim}$ is selected close to the mean period of the pathological oscillation. The stimulation frequency $f_{stim}=1/T_{stim}$ is selected in accordance with the prior knowledge familiar to the skilled person with respect to the pathological frequency bands characterized for the respective disease (that is in agreement with the pathological rhythms which should be desynchronized using the CR stimulation) or is adapted by means of feedback by measurement of the pathological neuronal activity to be desynchronized via sensors and a determination of the frequency peak in the pathological frequency band familiar to the skilled person. Furthermore, a literature value for the mean period of the pathological oscillation can be used and the period $T_{stim}$ used for the stimulation can differ from this literature value by e.g. up to ±5%, ±10% or ±20%.

Figure 6:
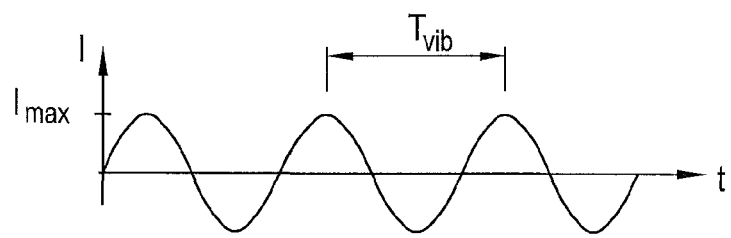
FIG. 6 illustrates a schematic representation of a vibration stimulus.

FIG. 6 shows as an example for the vibration V(t) a continuous sine oscillation of a frequency $f_{vib}=1/T_{vib}$ in the range from 0.25 to 300 Hz, in particular in the range from 0.25 to 50 Hz or 100 to 300 Hz, where $T_{vib}$ is the period duration of the vibration stimulus. The vibratory stimuli can also have a different shape e.g. a rectangular shape, instead of a sine shape. The deflection $l_{max}$ of a respective stimulation element 35 for generating the vibration V(t) can lie in the range from 0.1 to 0.5 mm or up to 5 mm. At a frequency $F_{vib}$ of 300 Hz, a stimulation element 35 can exert a force of e.g. approximately 2 N onto the surface of the body of the patient.

In the event that thermal stimuli are to be applied by the stimulation elements 35, each stimulation element 35 can be configured such that it can generate a predefined temperature $T_{temp}$ on the surface of the body of the patient or in a lower-lying region. The temperature $T_{temp}$ can be above or below the temperature $T_0$ present in the target area without the application of the thermal stimulus, i.e. the target area can be heated or cooled. The temperature $T_{temp}$ can e.g. be in the range from 22 to 42° C. The temperature $T_0$ is as a rule the body temperature of the patient. In an embodiment, the stimulation elements 35 are the outputs of light guides that are in particular fed by a common laser. The laser light can be distributed over the light guides using a suitable control such that the desired application of thermal stimuli is achieved.

The total thermal signal of a stimulation element 35 is calculated from $P(t)H_{l,m}(t)$, where P(t) is the periodic sequence of pulses such as has been explained above in connection with FIG. 5, and $H_{l,m}(t)$ is formed analogously to $A_{l,m}(t)$ and indicates the temperature generated by each stimulation element 35 (at a respective l, m) at a given point in time t. The site is in particular indicated by $H_{l,m}(t)$ at which the activated group of stimulation elements 35 is located at the respective point in time t.

While the activation of the stimulation elements 35 e.g. migrates from left to right over the cuff 36 along a path, the phase entrainment is calculated in a sliding window between P(t) and the pathologically rhythmic neuronal activity. In this respect, regions on the surface of the body of the patient along the path are identified in which the phase synchronization between P(t) and the pathologically rhythmic neuronal activity of the stimulated neurons respectively has a local maximum. The window length should be selected such that it corresponds to at least 10, better 50 or even 100 mean periods of the pathological neuronal rhythm. The movement speed of the activation front $X_F(t)$ results from this. As the window length grows, the spatial resolution grows, but also the examination time. A multi-step procedure has also proven itself in practice: first scan large body areas with a smaller window length to roughly detect body points with good phase entrainment to then only scan these special body points in detail with a larger window length.

The starting point of the activated group of stimulation elements 35, this is the left margin of the cuff 36 in the examples of FIGS. 3 and 4, and the path the activation covers can adopt different shapes and can be selected in different manners. The shape of the activation group, i.e. the 3×3 group in the examples of FIGS. 3 and 4, can be predefined or can be set by the user, i.e. a physician, trained medical personnel or the patient, e.g. via corresponding switches. For example, pressure switches in the cuff 36 can be associated with each stimulation element 35 or smaller groups of stimulation elements 35 or the user can set the shape of the activation group via a tablet, e.g. an iPad or the like.

Figure 7:
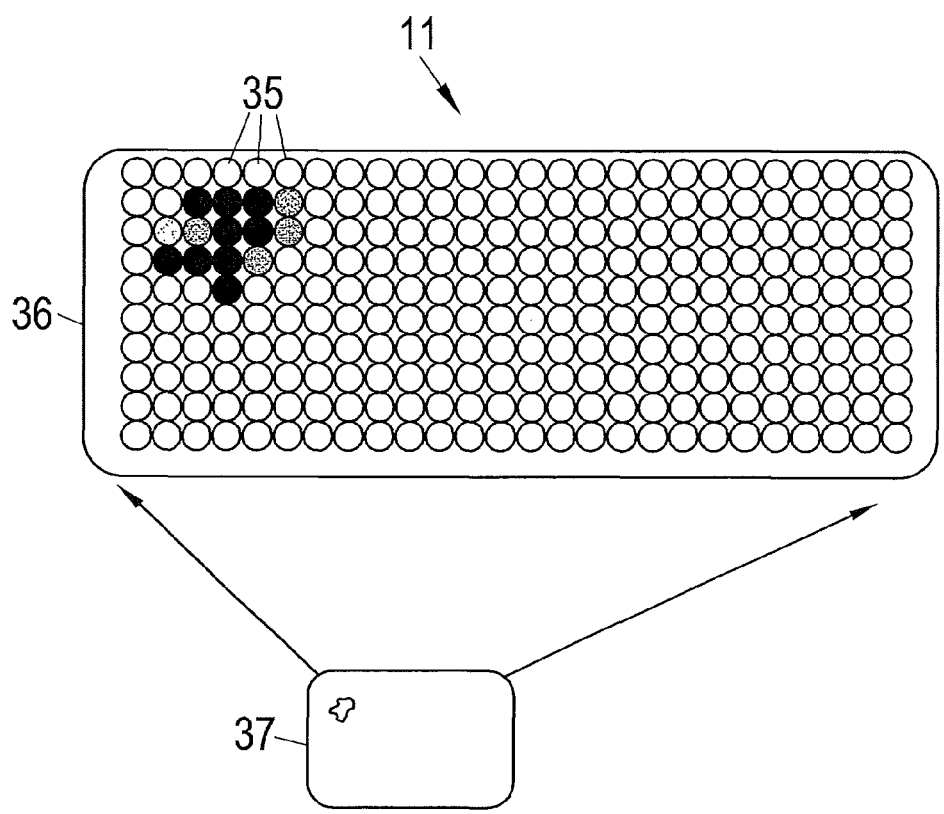
FIG. 7 illustrates a schematic representation of a selection of an activation group using a tablet.

FIG. 7 schematically shows a tablet 37, e.g. an iPad, via which the starting configuration of the activation group is set. For this purpose, a corresponding group is marked, e.g. by means of a touch screen, on the tablet 37. The associated stimulation elements 35 can optionally hereby be activated, whereby the user can see where the activation is taking place, e.g. from the feedback of the patient ("Where can you feel the activation?") or a flashing (only occurring during this test phase) of the LEDs belonging to the corresponding stimulation elements 35 on the cuff 36. The tablet 37 is preferably connected to the cuff 36 without a cable. Said cuff is connected to a battery and optionally also to a control unit for the patient. The control unit allows the patient to operate the cuff 36 in a simple manner without having to use the table 37 separately. The battery and the control unit can also be combined with the cuff 36 from a construction aspect.

The shape of the activation group can be slowly varied in accordance with an embodiment. The shape of the activation group can e.g. be slowly varied in that, starting from the focus, the activation group is stretched centrally by z %, where z is slowly varied from the starting value (100%) up to a maximum value, e.g. 110% at z=10. Analogously to the variation of the position of the activation front, the value of the stretch z is used in this case for the phase entrainment analysis instead of the position of the activation front. In this manner, configurations of the activation group can be automatically adapted to the individual anatomy and physiology of the patient, in particular the size of the receptive fields, and can thus be optimized.

The path of the activation group can be predefined or randomly selected or can be set by the user e.g. by means of pressure buttons in the cuff 36 or with the aid of the tablet 37. The user can e.g. for this purpose predefine a plurality of anatomically or physiologically preferred target positions on the tablet 37. The activation group subsequently moves over the route predefined by these sites and determined by means of the customary interpolation methods.

The selection of the sites or regions at which the stimuli intended for the therapy of the patient are applied takes place with the aid of an entrainment test. The entrainment test has the advantage over other tests that it is much faster and more sensitive. In addition, the low stimulus level in the entrainment test enables a larger anatomical accuracy since smaller neuronal populations are stimulated. This is important for the calibration of the CR stimulation since in this respect subpopulations are to be stimulated via the individual stimulation channels that are as separate as possible and are even disjunctive in the ideal case.

The entrainment test is based on the determination of the characteristic of a phase synchronization between a periodic stimulus and the neuronal rhythm of the pathologically synchronous and oscillatory neuronal population. The periodic sequence P(t), that is shown by way of example in FIG. 5, applies a stimulus at the times $\tau_1, \tau_2, \ldots, \tau_K$, where K is the number of stimuli. Since the order is periodic, the stimulation period $T_{stim}$ is constant, i.e. $T_{stim}=\tau_{j+1}-\tau_j$ applies to all $j=1, \ldots, K-1$. The associated stimulation frequency, i.e. repetition rate, is $f_{stim}=1/T_{stim}$.

The phase of the periodic stimulation sequence P(t) is $\varphi_1(t)=2\pi(t-\tau_1)/T_{stim}$ (cf. e.g. M. G. Rosenblum, A. S. Pikovsky, C. Schäfer, J. Kurths, P. A. Tass: Phase Synchronization: From Theory to Data Analysis. In: Moss F. (Ed.): Handbook of Biological Physics, Elsevier (2000)). The phase thus selected disappears when the first stimulus is applied: $\varphi_1(t)=0$.

Alternatively, a phase shift can also be "built in" which does not change anything in the results and also does not bring about any advantages. A phase shift can be "built in" in that either a different starting time is selected $\varphi_1(t)=2\pi(t-\xi)/T_{stim}$, where $\xi \neq \tau_1$ and $\xi$=const, or in that a phase shift $\vartheta$ is explicitly added thereto: $\varphi_1(t)=2\pi(t-\tau_1)/T_{stim}+\vartheta$, where c=const. The period $T_{stim}$ can also be a temporally slowly varying function of time: $T_{stim}=\chi(t)$. The period $T_{stim}$ can in particular be slowly varied in time in a deterministic or stochastic or mixed deterministic-stochastic manner, with the changes of the stimulation frequency $f_{stim}$ being at least one order of magnitude slower in comparison with the time scale of the oscillation to be examined.

The phase $\varphi_2(t)$ of the neuronal rhythm to be examined is determined from the measured signal 23 and in particular by means of Hilbert transformation from the signal that is determined by means of band pass filtering or by empirical mode decomposition and that represents the pathological oscillatory activity. The empirical mode decomposition allows, in contrast to band pass filtering, a parameter-independent determination of physiologically relevant modes in different frequency ranges (cf. N. E. Huang et al.: The empirical mode decomposition and the Hilbert spectrum for nonlinear and non-stationary time series analysis. Proc. R. Soc. A: Math. Phys. Eng. Sci. 454, 903-995 (1998)). The combination of empirical mode decomposition with a subsequent Hilbert transformation is called a Hilbert-Huang transformation (cf. N. E. Huang et al.; A confidence limit for the empirical mode decomposition and Hilbert spectral analysis. Proceedings of the Royal Society of London Series A 459, 2317-2345 (2003)). The phase $\varphi_2(t)$ of the neuronal rhythm to be examined can also be determined by means of wavelet analysis. In addition to the instantaneous (time-dependent) phase $\varphi_2(t)$ of the neuronal oscillation to be examined, its instantaneous (time-dependent) amplitude is additionally obtained in this manner.

To determine the degree of phase synchronization between the stimulus and the neuronal rhythm, we will look at the n:m phase difference between the stimulus and the neuronal rhythm $\psi_{n,m}(t)=n\varphi_1(t)-m\varphi_2(t)$, where n and m are small whole numbers. In this manner, the phase synchronization between the stimulus and a neuronal rhythm can be examined in different frequency bands. I.e. to examine the effect of the stimulation on neuronal rhythms, it is not necessary to restrict oneself to the rhythm which is in the same frequency range as the stimulus frequency (n=m=1). The n:m phase difference modulo $2\pi$ is $\Phi_{n,m}(t)=[n\varphi_1(t)-m\varphi_2(t)]_{mod\ 2\pi}$.

Inter alia determined by the sampling rate, the n:m phase difference modulo $2\pi$ is determined at the times $t_1, t_2, \ldots, t_N$. We thus obtain the association distribution $\Phi_{n,m}$ of that reads $\{\Phi_{n,m}(t_l)\}_{j=a}^{b}$: The distribution can include all the measured values of $\Phi_{n,m}(a=t_1, b=t_N)$ or only a subgroup ($a>t_1$ and/or $b<t_N$) to e.g. exclude transient effects from the analysis. For this purpose, e.g. the first approximately 10 stimuli are taken from the analysis.

If there is no n:m phase synchronization, the distribution of the n:m phase difference modulo $2\pi$ is an equal distribution (or comes sufficiently close thereto). In contrast to this, the n:m phase synchronization is characterized by the occurrence of one or more cluster points of $\Phi_{n,m}(t)$ (cf. P. Tass, M. G. Rosenblum, J. Weule, J. Kurths, A. Pikovsky, J. Volkmann, A. Schnitzler and H.-J. Freund: Detection of n:m Phase Locking from Noisy Data: Application to Magnetoencephalography. Phys. Rev. Lett. 81 (15), 3291-3294 (1998); M. G. Rosenblum, A. S. Pikovsky, C. Schäfer, J. Kurths, P. A. Tass: Phase Synchronization: From Theory to Data Analysis. In: Moss F. (Ed.): Handbook of Biological Physics, Elsevier (2000)).

The occurrence of an n:m phase synchronization can be determined by means of different variables. Examples will be shown in the following:

(i) If the distribution of $\Phi_{n,m}$ has a (single) cluster value, the circular mean value of this distribution can be calculated:

$$S_{n,m} = \left| \frac{1}{b-a+1} \sum_{l=a}^{b} \exp[i\Phi_{n,m}(t_l)] \right|$$

where $0 \leq S_{n,m} \leq 1$ and an equal distribution results in $S_{n,m}=0$ while a perfect phase synchronization is characterized by $S_{n,m}=1$ (cf. M. G. Rosenblum, A. S. Pikovsky, C. Schäfer, J. Kurths, P. A. Tass: Phase Synchronization: From Theory to Data Analysis. In: Moss F. (Ed.): Handbook of Biological Physics, Elsevier (2000)). The disadvantage of this synchronization index is that it typically does not deliver any sensible results if the distribution $\{\Phi_{n,m}(t)\}_{j=a}^{b}$ has more than one cluster value. If e.g. it has two out-of-phase cluster values, a value of $S_{n,m}$ close to zero results.

(ii) A synchronization index should therefore additionally (or exclusively) be calculated which delivers reliable results independently of the number of cluster values. For this purpose, the Kuiper test, the circular variant of the Kolmogorov-Smirnov test (cf. E. Batschelet: Circular Statistics in Biology (Academic Press, London, 1981); N. H. Kuiper: Tests concerning random points in a circle. Proc. K. Ned. Akad. Wet., Ser. A: Math. Sci. 63, 38 (1960); P. A. Tass: Transmission of stimulus-locked responses in two coupled phase oscillators. Phys. Rev. E 69, 051909-1-24 (2004)), is used to determine the probability with which the distribution $\{\Phi_{n,m}(t)\}_{j=a}^{b}$ is an equal distribution. A P value is then obtained which is the smallest significance level at which the zero hypothesis (that the observed distribution $\{\Phi_{n\ m}(t)\}_{j=a}^{b}$ is an equal distribution) can be rejected. If $\{\Phi_{n,m}(t)\}_{j=a}^{b}$ is an equal distribution P=1 results. If, in contrast, $\{\Phi_{n,m}(t)\}_{j=a}^{b}$ has a single, considerably pronounced cluster value, a P value close to 0 is obtained.

(iii) A further possibility is an n: m synchronization index $\rho_{n,m}$ based on the Shannon entropy of the distribution $$\{\Phi_{n,m}\}_{j=a}^{b} \cdot \rho_{n,m} = \frac{S_{max} - S}{S_{max}}$$

results with an estimate $p_k$ of the distribution $p_k$ $\{\Phi_{n,m}(t)\}_{j=a}^{b}$, where $$S = -\sum_{k=1}^{L} p_k \ln p_k.$$

The maximum entropy is $S_{max}$=1 nL, where L is the number of bins and $p_k$ is the relative frequency at which $\Phi_{n,m}$ is found in the kth bin (cf. P. Landa: Nonlinear Oscillations and Waves in Dynamical Systems. Kluwer Academic Publishers, Dordrecht-Boston-London, 1996). $0 \leq \rho_{n,m} \leq 1$ applies due to the normalization. With an equal distribution, that is with the complete lack of an n:m phase synchronization, $\rho_{n,m}$=0 results, while a perfect n:m phase synchronization produces a Dirac-like distribution (i.e. all values of $\Phi_{n,m}$ are in the same bin), so that $\rho_{n,m}$=1. In comparison with the n:m synchronization index listed under (ii) and based on the Kuiper test, the n:m synchronization index $\rho_{n,m}$ based on the Shannon entropy has the disadvantage that its value depends on the exact position of the cluster value with more pronounced cluster values of the distribution so that artificial oscillations result with a cyclic shift of the cluster value in the interval [0,2π] (cf. P. A. Tass: Transmission of stimulus-locked responses in two coupled phase oscillators. Phys. Rev. E 69, 051909-1-24 (2004)).

In addition to the stimulation-induced effects on the phase $\varphi_2(t)$ of the neuronal rhythm and thus the n:m phase difference $\varphi_{n,m}$ stimulation-induced effects on the amplitude A(t) of the neuronal rhythm are also examined. n and m result from the ratio of stimulation frequency $f_{stim}$ to the dominant spectral frequency peak. The analysis can, however, also be carried out as standard for some few pairs of n and m (in each case small and a whole number, e.g. n, m=1, 2, 3), e.g.: (n,m)=(1,1)=(1,2)=(2,1)=(2,3)=(3,2)= . . . . It is not only a question of whether the stimulation brings the neuronal rhythm in cycle in an n:m ratio, but rather whether the stimulation also changes the degree of the synchronization of the neurons underlying the neuronal rhythm. An increase in the synchronization within the stimulated neuronal population results in a growing of the amplitude A(t). Conversely, a decrease in the synchronization within the neuronal population underlying the neuronal rhythm produces a decrease of the amplitude A(t). Measurements in a comparison interval (e.g. before administering the stimulation) thus have to be carried out for the evaluation of the amplitude effects. Alternatively, amplitude effects can also simply be determined by an analysis of the power spectral density—of a predefined frequency band typical for the disease and familiar to the skilled person or of one or more empirical modes extracted from the data or by means of wavelet analysis.

To determine the significance of the phase effects or amplitude effects induced by the periodic stimulus sequence, a pre-stimulus baseline can be determined in a time window $F_{pre}$ having a length that corresponds to ten times to a thousand times the mean period of the oscillation to be examined.

For the baseline determination of the amplitude A(t) of the neuronal rhythm, the 99th percentile of this distribution or simply the maximum is e.g. taken as the baseline value for A(t) in the time window $F_{pre}$. If the signals are not of the best quality due to artifacts, because e.g. no artifact elimination has been connected upstream with EEG signals, a lower percentile can also be selected as the baseline (if the artifacts should have large amplitude values). Such a procedure is familiar to the skilled person.

A baseline of the n:m phase synchronization can e.g. be determined in that a sham stimulation is so-to-say carried out in the time window $F_{pre}$. I.e. an n:m phase synchronization is carried out with a virtual periodic stimulus sequence in the time window $F_{pre}$ in which no stimulation takes place. Another possibility for the determination would e.g. be to replace the real signals derived under stimulation with surrogate data and then to determine the n:m phase synchronization for this purpose. Such procedures are known to the skilled person.

Once activation groups, i.e. regions on the surface of the body of the patient, have been determined with the aid of the entrainment test in which regions the phase synchronization between the periodic application of the stimuli and the neuronal activity of the stimulated neurons is sufficiently high or has a local maximum, a pair test is carried out in which phase-resetting stimuli are applied in two different regions on the surface of the body of the patient to select effective pairs for the CR stimulation. The pair test is carried out directly after the entrainment test without ideal individual stimuli previously having been determined beforehand by means of a phase-resetting analysis.

FIG. 8 schematically shows a pair test. Activation groups. i.e. regions on the surface of the body of the patient, selected previously with the aid of the entrainment test are used here to apply mechanically tactile and/or thermal stimuli 40 in the respective region on the surface of the body of the patient. Due to the somatotopic association, the stimuli 40 applied in the selected regions stimulate a respective subpopulation of the neuronal population with the pathologically synchronous and oscillatory activity. The stimuli 40 are configured to reset the phase of the pathologically synchronous and oscillatory neuronal activity of the respectively stimulated subpopulation. If more than two activation groups were selected as the result of the entrainment test, the pair test is preferably carried out using respective adjacent activation groups.

The stimulation elements 35 in each of the two activation groups 1 and 2 generate the phase-resetting stimuli 40 periodically in a sequence having the period $T_{stim}$. In the present case, each sequence comprises three stimuli 40; however, the sequences can also include further stimuli 40.

A predefined break is observed after each sequence and the sequence is then repeated. The break, which can also be dispensed with, can in particular amount to a whole-number multiple of the period $T_{stim}$. The time delay between the sequences of different activation groups $T_{stim}/2$, i.e. the stimulation of activation group 2 is offset in time by $T_{stim}/2$ with respect to the stimulation of activation group 1 such that the stimulation of the respective subpopulations likewise takes place in a time-offset manner. The phases of the stimulated subpopulations is reset at different points in time due to this time offset. Except for the time offset, the stimulations carried out by activation groups 1 and 2 can e.g. be identical.

Whether effective stimulation can take place via a respective pair of activation groups is determined by the amplitude $A(t)$ of the pathological oscillation measured by the measuring unit 12. A pair-wise stimulation is deemed successful when no amplitude increase $A(t)$ of the pathological oscillation (that is no amplification of the synchronization of the pathologically synchronized neuronal population generating the signal) occurs or even when a slight decrease (corresponds to a weak desynchronization) occurs. I.e. the amplitude $A(t)$ of the neuronal rhythm may not increase in comparison with a baseline time window $F_{pre}$. The amplitude $A(t)$ should rather drop or at least remain unchanged in comparison with the baseline time window $F_{pre}$. The value of the amplitude $A(t)$ recorded under pair stimulation can e.g. be associated with a percentile of the distribution of the amplitude $A(t)$ in the baseline time window $F_{pre}$. Or corresponding relationships can be calculated.

A pair test is carried out either for all the possible pairs that can be formed from the selected activation groups or, since faster, e.g. along a preferential axis, e.g. along a belt worn on the stomach or proceeding from the fingers in the direction of the shoulders, from the first activation group to the next activation group that is next suitable—and from this then to the then next, etc. This saves time. The best groups of three, four, five, six (etc. e.g. up to ten) comprising 3, 4, 5, 6, . . . , 10 activation groups, i.e. regions on the surface of the body of the patient can also e.g. be extracted from the matrix of all the pair comparisons. Unsuitable pairs of activation groups that e.g. amplify the pathological neuronal synchronization are replaced with more suitable pairs.

The groups determined in this manner are examined with respect to their effectiveness in the group test. An exemplary group test of a group comprising four activation groups is shown by way of example in FIG. 9. Each activation group comprising the respective stimulation elements 35 applies, in exactly the same way as in the pair test, a sequence of phase resetting stimuli 40 in the respective region on the surface of the body of the patient. The phase resetting stimuli 40 are applied periodically within a sequence with the period $T_{stim}$. In the present example, each sequence comprises three stimuli 40; however, the sequences can also include more stimuli 40. A specific break is observed after each sequence and the sequence is then repeated. The break can alternatively also be dispensed with. The time delay between the sequences of adjacent activation groups furthermore amount to $T_{stim}/4$ since four activation groups are tested in the group test. For the general case of N activation groups, the time delay of adjacent channels would amount to $T_{stim}/N$. It is furthermore possible that the order in which the activation groups generate the stimuli 40 is varied. Furthermore, the stimuli 40 generated by the N activation groups can e.g. be identical.

The control and analysis unit 10 checks whether the pathologically synchronous and oscillatory neuronal activity of the stimulated neurons is suppressed and is in particular desynchronized on the application of the stimuli 40 over the selected group of activation groups. The effectiveness of the CR stimulation over the groups determined as described above is determined using the amplitude criterion described as in the pair test and/or by means of a clinical determination, e.g. by means of clinical scores or a simple clinical observation by an experienced physician or other therapist. If none of the selected groups are effective, new groups have to be localized using the pair matrix or the full pair matrix has to be determined.

In accordance with an embodiment, the pair test is dispensed with and a group test is immediately carried out after the end of the entrainment test. All the activation groups, e.g. four activation groups, selected in the course of the entrainment test are used to apply a CR stimulation. The stimulation success can in particular be checked by means of a threshold value comparison. Depending on which signals are used for determining the stimulation success, different threshold value comparisons result. If e.g. the pathologically neuronal synchronization is measured via the sensors of the measuring unit 12, e.g. EEG electrodes or deep electrodes (as an LFP signal), experience has shown that the lowering of the synchronization by e.g. at least 20% in comparison with the situation without stimulation is sufficient to determine a sufficient stimulation success. In accordance with an embodiment, an insufficient stimulation success can be determined if the pathologically neuronal synchronization by the application of the stimuli 40 is not reduced by at least a predefined value. If symptoms of the patient are used for determining the stimulation success, which reduction is to be considered as a clinically relevant improvement depends on the kind of clinical parameters used. Such reduction values (e.g. in the sense of the so-called minimal clinically perceptible improvement) are familiar to the skilled person.

In another embodiment, starting from a suitable (starting) activation group, this is activation group 1 by way of example in FIG. 10, a second activation group, this is activation group 2 by way of example in FIG. 10, is introduced and is moved slowly away from the starting activation group (as in FIG. 10) or toward it (not drawn). The stimulation shown in FIG. 8 is carried out in the meantime with which the regions on the surface of the body of the patient covered by the activation groups 1 and 2 at a respective point in time are stimulated. The path of the movement can in this respect be predefined or can be set by the user as explained above. The starting point of activation group 2 can be close to activation group 1 or can coincide with the starting point of activation group 1. A suitable distance of both activation groups is recognized by a good stimulation effect (electrophysiologically a good desynchronization or clinically a good symptom reduction). As soon as this is reached, the spacing should not be further increased in order to be able to utilize a sufficiently large number of activation groups for the following therapeutic stimulation.

Two paths can now be taken in principle in an iterative manner in this method. A first possibility is the pair-wise testing of further suitable pairs of activation groups, i.e. the just determined activation group 2 becomes the new starting activation group, as is shown in FIG. 11, and a further activation group, namely activation group 3, is added. Activation group 3 is slowly moved away from or toward starting activation group 2, with the stimulation shown in FIG. 8 being carried out (with N=2) by activation groups 2 and 3 until it is found with reference to the measured signals 23 recorded by the measuring unit 12 that a good stimulation effect is achieved, i.e. that a good desynchronization observed e.g. with the aid of the measuring unit is present. The starting point of activation group 3 can be close to activation group 2 or can coincide with the starting point of activation group 3. If finally all the suitable pairs of activation groups have been successively determined, a CR stimulation is carried out using all these activation groups as well as subgroups of activation groups, as is shown in FIG. 9. The group or subgroup that delivers the best results is selected for the following therapeutic stimulation.

It is faster for the practical application if the number of activation groups is extended iteratively. In the example of FIG. 10 the two activation groups 1 and 2 determined as suitable are set. An activation group 3 is added and its spacing along a predefined path or along a path selected by the user varies, as is shown by way of example in FIG. 12. Activation group 3 is slowly moved away from or toward starting activation group 2, with the stimulation shown in FIG. 9 being carried out in the meantime (with N=3 since stimulation is performed with three activation groups) until it is found with reference to the measured signals 23 recorded by the measuring unit 12 that a good stimulation effect is achieved, i.e. that a good desynchronization observed e.g. with the aid of the measuring unit 12 is present. The starting point of activation group 3 can be close to activation group 2 or can coincide with the starting point of activation group 3. In contrast to the pair-wise testing shown in FIG. 11, all the previously determined activation groups are retained in the embodiment shown in FIG. 12. The total body part covered by the cuff 36 is finally covered with activation groups in this manner. The configuration hereby obtained is used for the following therapeutic stimulation.

Different analysis methods are familiar to the skilled person to check whether the stimuli 40 applied in the embodiments in accordance with FIGS. 8 to 12 reset the phase of neuronal activity. The analysis of the phase resetting of the synchronous neuronal activity typically takes place by means of an ensemble of identical stimuli. A possibility familiar to the skilled person for analyzing the phase reset comprises a phase resetting analysis such as is described in the article "Stochastic phase resetting of two coupled phase oscillators stimulated at different times" by P. A. Tass (printed in Physical Review E 67, 2003, pages 051902-1 to 051902-15). The phase resetting index is determined for this purpose (cf. equation 8, stimulus locking index for $\vartheta=1$). The phase used in this respect for calculating the phase reset is e.g. determined by means of Hilbert transformation from the signal that is determined by means of band pass filtering or empirical mode decomposition and that represents the pathological oscillatory activity (the latter enables in comparison with band pass filtering a parameter-independent determination of physiologically relevant modes in different frequency ranges, cf. "The empirical mode decomposition and the Hilbert spectrum for nonlinear and non-stationary time series analysis" by N. E. Huang et al. (printed in Proceedings of the Royal Society of London Series A, 1998, Vol. 454, pages 903 to 995); the combination of empirical mode decomposition with a subsequent Hilbert transformation is called a Hilbert-Huang transformation (cf. "A confidence limit for the empirical mode decomposition and Hilbert spectral analysis" by N. E. Huang et al. (printed in Proceedings of the Royal Society of London Series A, 2003, Vol. 459, pages 2317 to 2345). A phase reset is achieved when the phase resetting index exceeds the 99th percentile of the prestimulus distribution of the phase resetting index (cf. FIG. 4 in "Stochastic phase resetting of two coupled phase oscillators stimulated at different times" by P. A. Tass). If a stronger phase resetting effect is medically desirable, higher thresholds can also be selected, e.g. twice to three times the 99th percentile of the prestimulus distribution of the phase resetting index.

Alternatively to this data analysis, simpler data analysis processes can also be used which are able to approximate the detection of phase resetting with a sufficient precision in practice. E.g. averaging can take place simply via the ensemble of stimulus responses. A phase resetting is then approximately to be assumed when the maximum amount of the stimulus response exceeds the 99th percentile of the prestimulus distribution of the averaged response (or double or three times it) (cf. FIG. 6 in "Stochastic phase resetting of two coupled phase oscillators stimulated at different times" by P. A. Tass, Phys. Rev. E 67, 051902-1 to 051902-15 (2003)).

Figure 13:
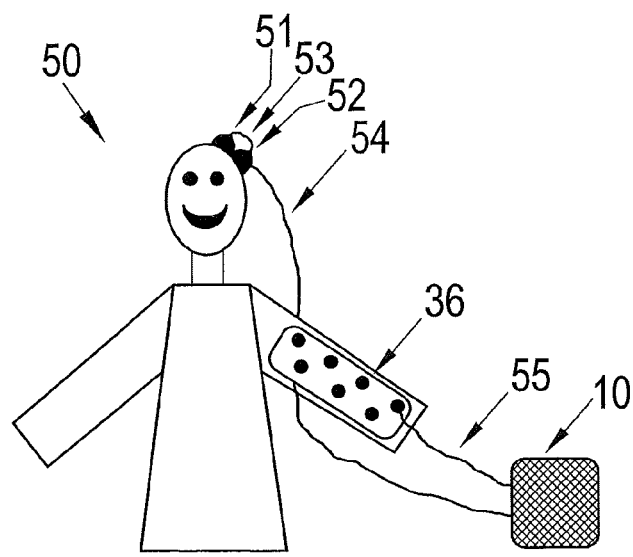
FIG. 13 illustrates a schematic representation of an apparatus for calibrating a mechanically tactile and/or thermal CR stimulation using a cuff fixed to the lower arm of the patient.

FIG. 13 schematically shows an apparatus 50 for an EEG-based calibration of a mechanically tactile and/or thermal CR stimulation. Non-invasively fixed EEG electrodes 51, 52, which are connected via a cable 53, serve as a measuring unit and measure the EEG stimulus responses which are passed on over a cable 54 to the central control and analysis unit 10. A cuff 36 having an array of stimulation elements 35 is fixed by hook-and-loop fasteners to the lower arm of the patient. The activation groups selected by means of the above-described calibration are marked by dots. The cuff 36 is connected via a cable 55 or telemetrically to the control and analysis unit 10 accommodating the battery or rechargeable battery. In the case of a telemetric connection, the cuff 36 also accommodates a battery or rechargeable battery.

Figure 14:
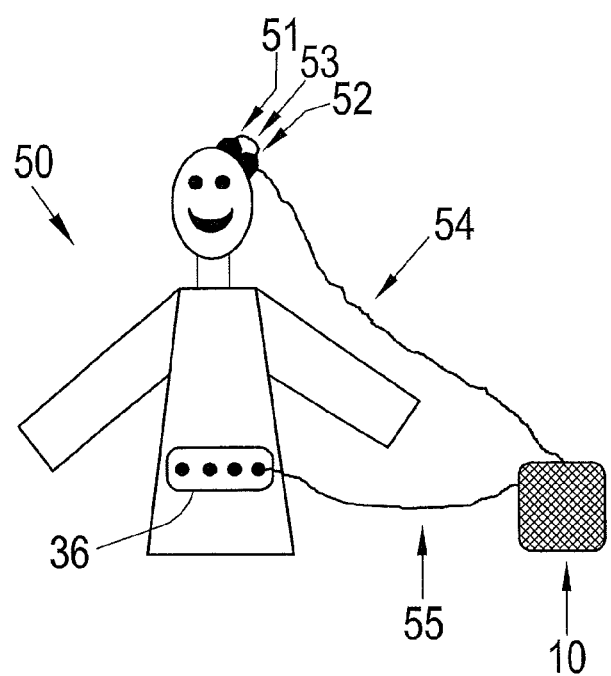
FIG. 14 illustrates a schematic representation of an apparatus for calibrating a mechanically tactile and/or thermal CR stimulation using a cuff fixed to the stomach of the patient.

FIG. 14 shows the apparatus 50 of FIG. 13, with the cuff 36 here being fastened to the stomach of the patient in the form of a belt.

The invention claimed is:

1. An apparatus for stimulating neurons, the apparatus comprising:
a non-invasive stimulation unit configured to apply at least one of a mechanically tactile and a thermal stimuli to a surface of a body of a patient, wherein the stimuli is applied to stimulate neurons having a pathologically synchronous and oscillatory neuronal activity;
a measuring unit configured to record measured signals that reproduce a neuronal activity of the stimulated neurons; and
a control and analysis unit configured to control the stimulation unit and to analyze the measured signals, wherein the control and analysis unit is further configured to automatically perform an entrainment test during which the control and analysis unit is configured to:
control the stimulation unit to raster scan at least a part of the surface of the body of the patient along a path and to periodically apply the stimuli to migrate over the surface of the body of the patient during the raster scan,
receive measured signals recorded by the measuring unit which reproduce the neuronal activity of the stimulated neurons during the raster scan,
calculate a phase synchronization between the measured signals and the periodic application of the stimuli during the raster scan,
determine at least two local maxima in the calculated phase synchronization, and
select at least two regions on the surface of the body of the patient along the path based on the measured signals recorded in response to the periodic application of the stimuli and the determined at least two local maxima, such that the phase synchronization between the periodic application of the stimuli and the neuronal activity of the stimulated neurons respectively has a local maximum in the selected at least two regions, respectively; and the control and analysis unit is further configured to perform a coordinated reset stimulation during which the stimulation unit is configured to apply the stimuli in the at least two regions that affect a phase reset of the neuronal activity of the stimulated neurons.

2. The apparatus in accordance with claim 1, wherein the control and analysis unit is further configured to determine based on the measured signals recorded in response to the stimuli applied in a time-offset manner whether the stimuli applied reduces the pathologically synchronous and oscillatory activity of the stimulated neurons.

3. The apparatus in accordance with claim 1, wherein the at least two regions selected by the control and analysis unit based on the periodic application of the stimuli comprise a first region and a second region, and wherein the control and analysis unit is further configured to displace the second region on the surface of the body of the patient if the control and analysis unit determines based on the measured signals recorded in response to the stimuli applied in a time-offset manner that the stimuli applied in the time-offset manner have not reduced the pathologically synchronous and oscillatory activity of the stimulated neurons.

4. The apparatus in accordance with claim 3, wherein the control and analysis unit is further configured to displace the second region on the surface of the body of the patient until the control and analysis unit determines based on the measured signals recorded in response to the stimuli applied in the time-offset manner that the stimuli applied have reduced the pathologically synchronous and oscillatory activity of the stimulated neurons.

5. The apparatus in accordance with claim 4, wherein the control and analysis unit is further configured to select a third region on the surface of the body of the patient after the application of the time-offset stimuli in the first and second regions and to control the stimulation unit to apply the stimuli in the time-offset manner in the second region and in the third region, and not in the first region, where the applied stimuli are configured to effect a phase reset of the neuronal activity of the stimulated neurons.

6. The apparatus in accordance with claim 5, wherein the control and analysis unit is further configured to displace the third region on the surface of the body of the patient when the control and analysis unit determines based on the measured signals recorded in response to the stimuli applied in the time-offset manner in the second and third regions that the stimuli applied has not reduced the pathologically synchronous and oscillatory activity of the stimulated neurons.

7. The apparatus in accordance with claim 5, wherein the control and analysis unit is further configured to select one or more additional regions on the surface of the body of the patient after the application of the time-offset stimuli in the second and third regions and to control the stimulation unit to apply the stimuli in the time-offset manner in two of the selected additional regions, and not in other regions, where the stimuli is configured to effect a phase reset of the neuronal activity of the stimulated neurons.

8. The apparatus in accordance with claim 3, wherein the control and analysis unit is further configured to select a third region on the surface of the body of the patient after the application of the time-offset stimuli in the first and second regions and to control the stimulation unit to apply stimuli in the time-offset manner in the first region, in the second region and in the third region, where the stimuli is configured to effect a phase reset of the neuronal activity of the stimulated neurons.

9. The apparatus in accordance with claim 8, wherein the control and analysis unit is further configured to displace the third region on the surface of the body of the patient when the control and analysis unit determines based on the measured signals recorded in response to the stimuli applied in the time-offset manner in the first, second and third regions that the stimuli applied has not reduce the pathologically synchronous and oscillatory activity of the stimulated neurons.

10. The apparatus in accordance with claim 8, wherein the control and analysis unit is further configured to select one or more additional regions on the surface of the body of the patient after the application of the time-offset stimuli in the first, second and third regions and to control the stimulation unit to apply the stimuli in the time-offset manner in the first region, in the second region, in the third region, and in the one or more additional selected regions, the stimuli being configured to effect a phase reset of the neuronal activity of the stimulated neurons.

11. The apparatus in accordance with claim 1, wherein the stimulation unit comprises a plurality of stimulation elements that are arranged in an array and each configured to generate the at least one of mechanically tactile and thermal stimuli.

12. The apparatus in accordance with claim 11, further comprising an activation group that includes a portion of the plurality of stimulation elements that are located at least partly within a specific shape that can be mapped on the array, with the shape moving over the array on a movement of the activation group and the stimulation elements included in the activation group changing accordingly.

13. The apparatus in accordance with claim 12, wherein, when the stimulation unit raster scans at least a part of the surface of the body of the patient, the activation group is configured to migrate along the path over the array and the stimulation elements included in the activation group generate the periodic stimuli.

14. The apparatus in accordance with claim 12, further comprising an input unit configured to receive an input from a user indicating at least one of the shape of the activation group and the path along which the activation group migrates.

15. The apparatus in accordance with claim 11, wherein the stimulation elements arranged in the array are fastened to a cuff that is configured to be fixed to the body of the patient.

16. A method for the stimulation of neurons, the method comprising:

applying, by a non-invasive stimulation unit, at least one of a mechanically tactile and thermal stimuli to a surface of a body of a patient, wherein the applied stimuli are configured to stimulate neurons having a pathologically synchronous and oscillatory neuronal activity;

measuring signals that reproduce a neuronal activity of the stimulated neurons;

automatically performing an entrainment test comprising:
raster scanning, by the stimulation unit, at least a part of the surface of the body of the patient along a path and periodically applying stimuli to migrate over the surface of the body of the patient during the raster scanning;

receiving measured signals which reproduce the neuronal activity of the stimulated neurons during the raster scanning;

calculating a phase synchronization between the measured signals and the periodic application of the stimuli during the raster scan;

determining at least two local maxima in the calculated phase synchronization;

selecting at least two regions on the surface of the body of the patient along the path based on the measured signals in response to the periodic applying of the stimuli and the determined at least two local maxima, such that the phase synchronization between the periodic applying of the stimuli and the neuronal activity of the stimulated neurons respectively has a local maximum in the selected at least two regions, respectively; and performing a coordinated reset stimulation comprising:

applying, by the stimulation unit, stimuli in the at least two regions that affect a phase reset of the neuronal activity of the stimulated neurons, wherein the stimuli applied in the at least two regions are offset in time with respect to one another.

17. The method in accordance with claim 16, wherein the selected at least two regions comprise a first region and a second region, and the method further comprises displacing the second region on the surface of the body of the patient when, based on the measured signals, the applied stimuli in a time-offset manner have not reduced the pathologically synchronous and oscillatory activity of the stimulated neurons.

18. The method in accordance with claim 17, further comprising displacing the second region on the surface of the body of the patient until, based on the measured signals, the stimuli applied have reduced the pathologically synchronous and oscillatory activity of the stimulated neurons.

19. The method in accordance with claim 17, further comprising:

selecting a third region on the surface of the body of the patient after the applying the time-offset stimuli in the first and second regions; and applying, by the stimulation unit, the stimuli in the time-offset manner in the second region and in the third region, and not in the first region, where the applied stimuli are configured to effect a phase reset of the neuronal activity of the stimulated neurons.

20. A tangible, non-transitory computer program product for execution in a data processing system, the tangible, non-transitory computer program product including instructions for:

applying, by a non-invasive stimulation unit, at least one of a mechanically tactile and thermal stimuli to a surface of a body of a patient, wherein the applied stimuli are configured to stimulate neurons having a pathologically synchronous and oscillatory neuronal activity;

measuring signals that reproduce a neuronal activity of the stimulated neurons;

automatically performing an entrainment test comprising:

raster scanning, by the stimulation unit, at least a part of the surface of the body of the patient along a path and periodically applying stimuli to migrate over the surface of the body of the patient during the raster scanning;

receiving measured signals which reproduce the neuronal activity of the stimulated neurons during the raster scanning;

calculating a phase synchronization between the measured signals and the periodic application of the stimuli during the raster scan;

determining at least two local maxima in the calculated phase synchronization;

selecting at least two regions on the surface of the body of the patient along the path based on the measured signals in response to the periodic applying of the stimuli and the determined at least two local maxima, such that the phase synchronization between the periodic applying of the stimuli and the neuronal activity of the stimulated neurons respectively has a local maximum in the selected at least two regions, respectively; and performing a coordinated reset stimulation comprising:

applying, by the stimulation unit, stimuli in the at least two regions that affect a phase reset of the neuronal activity of the stimulated neurons, wherein the stimuli applied in the at least two regions are offset in time with respect to one another.

* * * * *